United States Patent [19]

Shawl et al.

[11] Patent Number: 4,871,871

[45] Date of Patent: Oct. 3, 1989

[54] PROCESS FOR THE PREPARATION OF AROMATIC MONO- AND POLYISOCYANATES

[75] Inventors: Edward T. Shawl, Wallingford; Haven S. Kesling, Jr., Drexel Hill, both of Pa.

[73] Assignee: Arco Chemical Technology, Inc., Wilmington, Del.

[21] Appl. No.: 266,607

[22] Filed: Nov. 3, 1988

[51] Int. Cl.$^4$ .............................................. C07C 71/00
[52] U.S. Cl. ................................................... 560/344
[58] Field of Search ........................................ 560/344

[56] References Cited

U.S. PATENT DOCUMENTS 2,773,086 12/1956 Slocombe et al. .
3,898,259 8/1975 Hearsey ............................... 560/344
3,936,484 2/1976 Rosenthal et al. .
4,223,145 9/1980 Hentschel et al. .

FOREIGN PATENT DOCUMENTS 1473821 2/1967 France .

OTHER PUBLICATIONS

Hofmann, Proc. Royal Soc. London, 9, 274 (1858).
Hofmann, Chem. Ber. 3, 653 (1870).
Iwakura et al., Bull. Tokyo Inst. Tech 13, 25 (1950); Chem. Abs. 44, 3924e (1950).
Bennet et al., J. Am. Chem. Soc. 75, 2101 (1952).

*Primary Examiner*—Alan Siegel
*Attorney, Agent, or Firm*—Delbert E. McCaslin

[57] ABSTRACT

An improved process is provided for the preparation of aromatic mono- and poly- isocyanates by the thermal decomposition of an aromatic bis dialkyl urea in solvent in the presence of a tertiary amine hydrohalide, such as pyridine hydrochloride, as a promoter for conversion of the urea groups to isocyanates.

15 Claims, No Drawings

PROCESS FOR THE PREPARATION OF AROMATIC MONO- AND POLYISOCYANATES

FIELD OF THE INVENTION

The present invention relates to an improved process for the preparation of aromatic mono- and polyisocyanates by heating in an inert solvent an aromatic bis dialkyl urea in the presence of a tertiary amine hydrohalide, such as pyridine hydrochloride, as a promoter to convert the urea groups to isocyanate groups and recovering the aromatic isocyanate from the reaction mixture.

BACKGROUND OF THE INVENTION

A number of processes have have been reported for the preparation of aromatic mono- and polyisocyanates by the vapor or solvent phase decomposition of substituted ureas.

The production of aromatic isocyanates from symmetrical bis aryl ureas in the presence of hydrogen chloride, phosphorus pentoxide or zinc chloride was described by A. Hofmann in the Proc. Royal Soc., London, Vol. IX, p. 274 (1858). By heating a mixture of diphenyl urea with phosphorus pentoxide, zinc chloride or gaseous HCl; Hofmann distilled phenyl isocyanate overhead. No details of the experimental procedure are presented and the yield of isocyanate is not given.

A. Hofmann, Chemisch Berichte, Vol. 3, pp. 653–658 (1870) described heating diphenyl urea in the presence of phosphorus pentoxide giving yields too small to be considered for the preparation of the isocyanate.

Subsequent work by Iwakura and Nagakubo reported in the Bulletin Tokyo Inst. Technol., Vol. 13, p. 25 (1950) and Chemical Abstracts, Vol.44, p. 3924e (1950) describes the preparation of an aromatic isocyanate (p-ethoxyphenylisocyanate) by heating a solution of bis aryl urea such as bis (p-ethoxyphenyl) urea in the presence of hydrogen chloride gas.

The vapor phase decomposition of bis aryl ureas at 350° C. and higher temperatures has been described by W. D. Bennet et al, Journ. Am. Chem. Soc., Vol. 75, p. 2101 (1952) and Slocombe et al in U.S. Pat. No. 2,773,086, Dec. 4, 1956 in the presence of gaseous HCl as a promoter. Yields are reported in the 60 to 70% range for the vapor phase reaction and only a 5% yield for liquid phase reaction. A carbamoyl chloride intermediate is formed.

The liquid phase decomposition of trisubstituted ureas to isocyanates has been described by van Landeghem et al, French Patent No. 1,473,821, Feb. 13, 1967; C. J. Hearsey, U.S. Pat. No. 3,898,259, Aug. 5, 1975 and Rosenthal et al in the U.S. Pat. No. 3,936,484, Feb. 3, 1976. van Landeghem shows thermal decomposition of trisubstituted ureas in an organic solvent having specified dielectric constants at 140° to 170° C. with long reaction times of from 6 to 10 hours and modest yields of 60 to 75%. A variety of catalysts are shown but not exemplified or claimed, and include metal salts, such as acetates, stearates, and linoleates of manganese, zinc, cobalt, chromium and vanadium, tertiary amine bases, such as aliphatic, cycloaliphatic, aromatic and mixed tertiary amines, aliphatic heterocyclic amines such as N-methylpiperidine or N, N'-dimethylpiperidine as well as aromatic heterocyclic amines such as pyridine and pyrimidine. Other nitrogen compounds such as imidazole are indicated as being suitable. However, under the reaction conditions described tertiary amines as shown by van Landeghem do not catalyze urea decomposition.

Rosenthal et al U.S. Pat. No. 3,936,484 discloses the thermal decomposition of di- and tri-substituted ureas to isocyanates at temperatures above 230° C. in a solvent and isocyanate yields of from 60 to 80%.

The Hearsey U.S. Pat. No. 3,898,259 describes the introduction of gaseous hydrogen chloride into the liquid phase urea decomposition reaction to give reduced reaction times with isocyanate yeilds of from 8–90%. An excess of gaseous HCl is employed and a by-product carbamoyl chloride intermidiate formed.

A. Hentschel et al U.S. Pat. No. 4,223,145, Sept. 16, 1980 discloses the formation of an HCl adduct of a trisubstituted urea using at most a 10% excess of HCl. This adduct is then decomposed in a closed system at from 80°–180° C.

Applicants have found that hydrohalide salts of tertiary amines are very effective promoters for the thermal decomposition of trisubstituted ureas to the corresponding isocyanates at relatively mild reaction temperatures using short residence times as an organic solvent. Although it has been shown that the hydrohalide acids (HCl) promote urea decomposition, it is unexpected that the salts of these acids, especially, tertiaryl amine salts of these acids would be effective promoters. The isocyanates obtained by the instant process are in obtained in nearly quantitative yield.

SUMMARY OF THE INVENTION

This invention relates to a novel improved process for the preparation of aromatic mono- and polyisocyanates from aromatic bis dialkyl ureas which comprises thermally treating the aromatic bis dialkyl urea which has been dissolved in or slurried with an inert organic solvent in the presence of a hydrohalide salt of a tertiary amine to produce the corresponding aromatic isocyanate. The aromatic isocyanates produced by the instant invention are of significant industrial importance and are particularly useful as intermediates in producing products for agricultural application and in the preparation of polyurethanes.

It is an object of the present invention, therefore, to provide an improved process for the production of aromatic mono- and polyisocyanates from trisubstituted ureas in high yield and high conversion of the ureas.

It is another object of this invention to provide an improved reaction (thermal decomposition) system for the conversion of aromatic bis (dialkyl) ureas to the corresponding aromatic isocyanates.

These and the other objects and advantages of this invention will become apparent from the description of the invention which follows, and from the claims.

DETAILED DESCRIPTION OF THE INVENTION

In accordance with the present invention aromatic mono- or polyisocyanates having the general formula $$Ar(NCO)_n$$

wherein Ar is a mono-, di- or polyvalent aromatic radical which may be substituted with a halogen group, ether group, nitro group or an alkyl group having from 1 to 10 carbon atoms and n is a integer of from 1 to 3 are produced by heating at temperatures of from about 50° C. to 220° C. preferably from about 90° C. to 150° C. an aromatic bis dialkyl urea having the general formula Ar(NHCONR'R")$_n$ wherein Ar is as described above and R' and R", which may be the same or different, are alkyl groups having from 1 to 10 carbon atoms and n is an integer of from 1 to 3 dissolved in or slurried in an organic solvent or mixture of solvents, which are stable and substantially chemically inert to the components of the reaction system, in the presence of a tertiary amine hydrohalide, such as pyridine hydrochloride, to convert the urea groups to isocyanates groups and the desired aromatic isocyanated product separated and recovered.

Referring to the general formulae set forth hereinabove Ar is preferably an aryl radical such as the mono-, di-, and trivalent radicals of benzene, toluene, naphthalene diphenyl, terphenyl and the like. The aryl radicals may carry from 1 to 3 dialkyl urea substitutents and may have hydrogen atoms at the other ring positions or they may be substituted by one or more groups such as an alkyl group having from 1 to 10 carbon atoms, a halogen radical, a nitro group, an ether group, or other groups which are non-reactive with the isocyanates produced and other components of the reaction system.

The R' and R" of the aromatic dialkyl urea formula set forth hereinabove may be substituted or unsubstituted mono-, di-, or trivalent radicals selected from saturated or monoolefinic unsaturated straight or branched chain aliphatic or cycloaliphatic radicals optionally containing alkoxyalkyl radicals with one or more ether linkages, aryl radicals, or aralkyl radicals. These radicals may be substituted with groups which are non-reactive with the isocyanates produced by the process of the invention, such as, for example, nitro or halo groups. Also included are cycloliphatic and substituted cycloaliphatic radicals containing from 5 to 7 carbon atoms such as cyclopentyl, cyclohexyl and cycloheptyl radicals. Representative dialkyl urea compounds which may be employed in the process of the present invention include, for example, N-phenyl-N', N'-dimethylurea, N-phenyl-N', N'-diethylurea, N-phenyl-N'-methyl-N'-ethylurea, N-phenyl-N', N'-dicyclohexylurea, 2,4-tolylene-(bisdiethylurea), 2, 6-tolylene-(bisdimethylurea), N-(2-chlorophenyl)-N', N'-bis (dicylohexyl) urea, m-phenylene bis (dimethylurea), 1, 5-naphthalene bis (dibutylurea) and the like. The urea compounds above described are merely representative of a large number of aromatic dialkyl ureas falling within the general formula above which can be converted to isocyanates in the solvent phase in the presence of a tertiary amine hydrohalide promoter.

Representative aryl isocyanates which may be produced by the process of the present invention include, for example, phenyl isocyanate, 4-chlorophenyl and 2-fluorophenyl isocyanates, m-tolyl isocyanate, m-trifluoromethylphenyl isocyanate, 3,4-dichlorophenyl isocyanate, m-phenylene diisocyanate, 2,4-tolylene diisocyanate, 2,6-tolylene diisocyanate, 1,5-naphthalene diisocyanate and the like compounds.

The tertiary amine hydrohalide salts employed in the process of the present invention to promote thermal decomposition of the ureas to the corresponding isocyanate may be prepared, for example, by reacting the tertiary amine selected with a hydrogen halide such as HCl. Salts of hydrogen fluoride, chloride, bromide or iodide may be used. The tertiary amines used to prepare the hydrohalide will conform to the general formula R,R',R"N wherein R,R' and R" are not hydrogen but may be an aliphatic radical having from 1 to 10 carbon atoms, a cycloaliphatic radical such as cyclopentyl, cyclohexyl and cycloheptyl radicals, an aromatic radical, or an aralkyl radical. Such radicals may be substituted with, for example, nitro or halo groups which are non-reactive with the isocyanate produced. Suitable amine salts include, for example, triethylamine hydrochloride, hydrobromide or hydrofluoride, trioctylamine hydrochloride, hydrobromide or hydrofluoride, N-methyl diethylamine hydrobromide or hydrochloride, N,N-di ethylaniline hydrochloride and N,N-dimethylcyclohexylamine hydrochloride. Hydrohalide salts of heterocyclic tertiary amines and heterocyclic aromatic amines may also be employed. Representative salts include, for example, N-methylpyrrolidine hydrochloride, pyridine hydrochloride or hydrobromide, 3-ethylpyridine hydrochloride, the hydrohalide salt of 1,4-diazabicyclo [2.2.2]octane, 4-chloropyridine hydrochloride, 4,4'-bipyridine dihydrochloride, quinoline hydrochloride or hydrobromide and the like. Salts of amine oxides such as 2-chloropyridine N-oxide hydrochloride may also be used as a promoter. In addition, the hydrohalide may be formed with an amine which may be part of a polymer such as polyvinyl pyridine or a resin prepared from tertiary amine groups attached to a styrene divinylbenzene polymer. The tertiary amine hydrohalide is generally employed in the process at a molar ratio of one to one based on the urea groups. However, an excess of the tertiary amine hydrohalide promoter may be used.

The process of the present invention can be suitably carried out by adding the aromatic bis dialkyl urea to a solvent or a mixture of solvents comprising the reaction medium. The urea may be soluble in the solvent or solvents or soluble at reaction temperature or the urea may be in the form of a slurry. Suitable solvents which may be employed include, for example, the aromatic hydrocarbons such as benzene, toluene, xylene, trimethylbenzene, tetrahydronaphthalene, as well as the higher alkyl-substituted aromatic hydrocarbons; alkanes and substituted alkanes as well as cycloalkanes having from 5 to 20 carbon atoms such as, for example, n-hexane, n-heptane, octane, nonane, cyclohexane, dodecane, octadecane, 2-methylhexane, 2-ethylhexane, methylcyclohexane, and the like; halogenated or nitrated aromatic and aliphatic hydrocarbons such as, for example, methylene chloride, carbon tetrachloride, 1,2-dichloroethane, tetrachloroethane, chlorobenzenes, nitrobenzenes, dinitrotoluene and the like; aromatic or aliphatic ethers such as, for example diphenylether, dibutylether, propyleneglycol dimethyl ether, and the like; tertiary amines, such as, for example, pyridine, triethylamine, N-methylpyrrolidone and the like.

The process of the present invention may be carried out as a batch, semi-continuous or continuous process and the order of addition of the materials and reactants may be varied to suit the particular apparatus employed. For example, in a batch process all the urea, the solvent and the tertiary amine hydrohalide may be charged together to the reaction vessel and then heated to reaction temperature, or, the tertiary amine hydrohalide and some solvent may be added to the reactor heated to the desired reaction temperature, and then the urea or the urea and additional solvent added to the mixture; the urea may be totally dissolved in the additional solvent or it may be added as a slurry in the solvent. The added materials can be maintained at any convenient temperature. In addition, the urea and solvent can be added to the reactor and then the tertiary amine hydrohalide added over a period of time by means of a solids addition apparatus. Depending of the choice of solvent and tertiary amine hydrohalide employed, the reaction product may be a single phase or it may have an organic phase and a salt phase. If the reaction product has two phases, the organic phase can be decanted from the salt phase. If the tertiary amine is higher boiling than the secondary amine by-product formed during reaction of the urea then the secondary amine can be recovered by fractional distillation and reused in synthesis of the urea. The tertiary amine salt may be regenerated and reused as a promoter for urea decomposition.

The reaction of the invention may be carried out in any suitable reactor which is equipped with a means for temperature control and agitation. Heating and/or cooling means may be employed interior or exterior of the reaction vessel to maintain temperature within the desired range.

As indicated hereinabove, the thermal decomposition of the aromatic bis dialkyl ureas is carried out at temperatures of from about 50° C. to about 220° C., preferably from about 90° C. to 150° C. Reaction time is dependent on decomposition temperature but will generally range between about 5 minutes and several hours. The reaction is generally carried out at atmospheric pressure, but depending on the boiling points of the solvents employed and the isocyanate product, it may be carried out at super-atmospheric or sub-atmospheric pressures. The isocyanate formed may be recovered by filtration, by distillation, or by other known methods depending on the solvent, tertiary amine salt employed and the isocyanate produced.

The present invention is more fully illustrated by the following examples, which include particular features of the invention. However, the examples are not to be construed as limiting the invention in any way, it being understood that numerous variations are possible without departing from the spirit and scope of the invention.

EXAMPLE 1 (comparative)

A mixture of 1.95 g (10.1 mmoles) of 1-phenyl-3, 3-diethylurea and 3.24 g, (43.2 mmoles) of pyridine in 100 g of o-xylene was added to a 250 ml round bottom flask fitted with a magnetic stirrer, condenser, and a thermocouple for measuring reaction temperature. A nitrogen atmosphere was maintained over the reaction mixture. The mixture was heated to 114° C. for 60 minutes. A sample was taken from the flask and analyzed by infrared spectroscopy. There was no peak for the NCO band in the spectrum. Another sample was taken and reacted with ethanol. Any phenyl isocyanate that would have been formed would be converted to the carbamate derivative. This sample was then analyzed by high pressure liquid chromatography (HPCL). Only unreacted starting material was observed confirming that no thermal decomposition of the urea to isocyanate occurred.

EXAMPLE 2 (comparative)

The procedure of Example 1 was repeated using 1.92 g (10.0 mmoles) of 1-phenyl-3, 3-diethylurea, 2.30 g pyridine and 100 g of mesitylene. The mixture was heated at 160° C. for 120 minutes. Analysis by infrared spectroscopy and HPCL showed no formation of isocyanate.

EXAMPLE 3

A mixture of 1.92 g (10 mmoles) of 1-phenyl-3, 3-diethylurea and 2.30 g (20 mmoles) of pyridine hydrochloride in 100 g o-xylene was heated for 30 minutes at 142° C. using the apparatus described in Example 1. Conversion of the 1-phenyl-3, 3-diethylurea was 90% and selectivity to the phenyl isocyanate, analyzed by HPCL as the ethyl carbamate was 99%.

EXAMPLE 4

A mixture of 19.2 g of 1-phenyl-3, 3-diethylurea and 7.6 g pyridine hydrochloride in 500 g of o-xylene was heated for 90 minutes at 140° C. in a 1000 ml round bottom flask equipped with a mechanical stirrer and condenser. At the end of the reaction, the organic phase was decanted from the salt phase and the salt phase was extracted with hot o-xylene. Analysis of the combined organic product and extract showed 96% conversion of the urea and 98% selectivity to the phenyl isocyanate. The phenyl isocyanate was recovered from the organic phase by fractional distillation. The salt phase was slurried in o-xylene and an additional 16 g pyridine was added The diethylamine by-product formed was then recovered from this slurry by fractional distillation. Diethylamine recovery in the distillation overhead was 85%.

EXAMPLE 5

A mixture of 32 g 2,4-tolylene (bisdiethylurea) and 35 g pyridine hydrochloride in 500 g o-xylene was heated at reflux for 90 minutes in a 1 liter fluted flask equipped with a mechanical stirrer and condenser. The product was cooled and then the organic phase was decanted from the salts. Conversion of the tolylene (bisdiethylurea) was 99% with selectivity of 95% to 2,4-toluene diisocyanate and 3% to the monoisocyanate monodiethylurea derivatives. Toluene diisocyanate was isolated by distillation from the xylene solution. The isolated product, 16 g, corresponded to a 92% overall yield.

EXAMPLES 6-13

A number of runs were made in accordance with the procedure of Example 3, utilizing various aromatic urea compounds, tertiary amine hydrohalide salts, solvents and conditions. Reaction materials, conditions and analytical results are set forth in the table below.

TABLE

EXAMPLES 6-13

| Ex. No. | Urea (g)* | Amine* Salt (g) | Solvent (g) | Temp. (°C.) | Time (Min) | Conversion of Urea (%) | Selectivity Mono NCO | DiNCO |
|---|---|---|---|---|---|---|---|---|
| 6 | DEPU (19.2) | py. HCl (14) | Toluene (120) | 110 | 90 | 98 | 97 | — |
| 7 | 80%/20% mix 2,4-TBDEU 2,6-TBDEU (3.2) | py.HBr (4.8) | Diphenylether (100) | 150 | 60 | 95 | 2 | 96 |
| 8 | DEPU (1.9) | 4-Cl py. HCl (1.65) | Xylene (100) | 142 | 90 | 85 | 92 | — |

TABLE-continued

EXAMPLES 6-13

| Ex. No. | Urea (g)* | Amine* Salt (g) | Solvent (g) | Temp. (°C.) | Time (Min) | Conversion of Urea (%) | Selectivity Mono NCO | DiNCO |
|---|---|---|---|---|---|---|---|---|
| 9 | DMPU (1.4) | Me3NHCl (1.9) | Hexadecane (150) | 160 | 30 | 70 | 85 | — |
| 10 | DEPU (1.9) | 2-Cl py. N—O (3.3) | Tetrachloro-ethane (100) | 100 | 60 | 75 | 84 | — |
| 11 | 2,4-TBDEU (3.2) | py. HCl (4.8) | Toluene (100) | 90 | 60 | 85 | — | 99 |
| 12 | 2,4 TBDMU (2.6) | py. HCl (3.2) | Mesitylene (100) | 162 | 90 | 99 | 1 | 97 |
| 13 | 2,4-TBDBU (4.3) | Mepyr. HCl (3.5) | Diphenylether (150) | 100 | 120 | 80 | 25 | 74 |

*DMPU = 1-phenyl-3, 3-dimethylurea
DEPU = 1-phenyl-3, 3-diethylurea
2,4-TBDEU = 2,4-tolylenebis (diethylurea)
2,4-TBDMU = 2,4-tolylenebis (dimethylurea)
2,4-TBDMU = 2,4-tolylenebis (dibutylurea)
2,6-TBDEU = 2,6-tolylenebis (diethylurea)
4Clpy. HCl = 4-chloropyridine hydrochloride
2ClpyN—O = 2-chloropyridine -N—oxide hydrochloride
py. HCl = pyridine hydrochloride
py. HBr = pyridine hydrobromide
Me3NHCl - trimethylamine hydrochloride
Mepyr. HCl = N—methylpyrrolidine hydrochloride

We claim:

1. A process for the preparation of an aromatic mono- or poly-isocyanate having the formula;

Ar(NCO)$_n$ wherein Ar is a mono-, di- or poly-valent aromatic radical which may be substituted with a halogen, ether, or nitro group or an alkyl group having from 1 to 10 carbon atoms and n is an integer of from 1 to 3 which comprises heating at a temperature within the range of from about 50° C. to about 220° C. an aromatic bis dialkyl urea having the formula Ar(NHCONR'R")$_n$ wherein Ar is as above described and R' and R" which may be the same or different, are an alkyl group having from 1 to 10 carbon atoms which may be substituted or unsubstituted mono-, di-, or tri-valent radicals selected from saturated or monoolefinic unsaturated straight or branched chain aliphatic or cycloaliphatic radicals and n is an integer of from 1 to 3, dissolved in or slurried in an organic solvent or mixture of solvents and in the presence of a tertiary amine hydrohalide as a promoter to convert the urea to the corresponding isocyanate, and thereafter separating and recovering the isocyanate.

2. A process according to claim 1 wherein the temperature is in the range of from 90° C. to 150° C.

3. A process according to claim 1 wherein the aromatic bis (dialkyl) urea is selected from the group consisting of 1-phenyl-3, 3-diethyl urea,1-phenyl-3, 3-dimethyl urea, 2,4-tolylene-bis (diethylurea), 2,6-tolylenebis (diethylurea), 2,4-tolylenebis (dimethylurea), and 2,6-tolylenebis (dibutylurea).

4. A process according to claim 3 wherein the aromatic bis (dialkyl) urea is a mixture of 2,4-tolyenebis (diethylurea) and 2,6-tolylenebis (diethylurea).

5. A process according to claim 1 wherein the tertiary amine hydrohalide is selected from the group consisting of pyridine hydrochloride, pyridine hydrobromide, 4-chloropyridine hydrochoride, 2-chloropyridine-N-oxide hydrochloride, trimethylamine hydrochloride and N-methylpyrrolidane hydrochloride.

6. A process according to claim 5 wherein the tertiary amine hydrohalide is pyridine hydrochloride.

7. A process according to claim 1 wherein the organic solvent is selected from the group consisting of toluene, o-xylene, diphenyl ether, hexadecane, tetrachloroethane and mesitylene.

8. A process according to claim 7 wherein the organic solvent is o-xylene.

9. A process for the preparation of 2,4-tolylene diisocyanate which comprises heating at a temperature in the range of from about 90° C. to about 150° C., 2,4-tolylenebis (diethylurea) in an organic solvent or mixture of solvents in the presence of a tertiary amine hydrohalide and separating and recovering the 2,4-tolylene diisocyanate from the reaction mixture.

10. A process according to claim 9 wherein the tertiary amine hydrohalide is pyridine hydrochloride and the solvent is toluene.

11. A process for the preparation of a mixture of 2,4- and 2,6-tolylene diisocyanate which comprises heating at a temperature in the range of from about 90° C. to about 150° C. a mixture of 2,4- and 2,6-tolylenebis (diethylurea) in an organic solvent or mixture of solvents in the presence of a tertiary amine hydrohalide and separating and recovering the mixture of 2,4- and 2,6-tolylene diisocyanates from the reaction mixture.

12. A process according to claim 11 wherein a mixture of about 80% 2,4-tolylenebis (diethylurea) and 20% 2,4-tolylenebis (diethylurea) is employed.

13. A process according to claim 1 wherein the molar ratio of tertiary amine hydrohalide to urea groups is 1:1.

14. A process according to claim 9 wherein the molar ratio of tertiary amine hydrohalide to urea groups is 1:1.

15. A process according to claim 11 wherein the molar ratio of tertiary amine hydrohalide to urea groups is 1:1.

* * * * *